United States Patent [19]

Crivello

[11] Patent Number: 4,535,174

[45] Date of Patent: Aug. 13, 1985

[54] FREE-RADICAL INITIATORS AND METHOD FOR MAKING

[75] Inventor: James V. Crivello, Clifton Park, N.Y.

[73] Assignee: General Electric Company, Schenectady, N.Y.

[21] Appl. No.: 667,931

[22] Filed: Nov. 2, 1984

[51] Int. Cl.$^3$ .............................. C07F 7/08; C07F 7/18
[52] U.S. Cl. ..................................... 556/443; 556/464
[58] Field of Search .............................. 556/443, 464

[56] References Cited

U.S. PATENT DOCUMENTS

| | | | |
|---|---|---|---|
| 3,256,308 | 6/1966 | Sterling et al. | 556/464 |
| 3,337,598 | 8/1967 | Sterling et al. | 556/464 |
| 3,433,819 | 3/1969 | Braun | 556/464 |
| 3,792,126 | 2/1974 | Vio | 260/880 R |
| 3,839,383 | 10/1974 | Kotzsch et al. | 556/464 |
| 3,931,355 | 1/1976 | Rudolph et al. | 260/865 |
| 4,145,507 | 3/1979 | Wolfers et al. | 556/443 X |
| 4,430,504 | 2/1984 | Reuter et al. | 556/482 |

FOREIGN PATENT DOCUMENTS

| | | | |
|---|---|---|---|
| 0083013 | 12/1982 | European Pat. Off. | 556/443 |
| 1044080 | 11/1958 | German Democratic Rep. | 556/464 |
| 2113296 | 9/1972 | German Democratic Rep. | 556/464 |
| 2088398 | 6/1982 | United Kingdom | 556/443 |

OTHER PUBLICATIONS

Calas et al., C. R. Acad. Sc. Paris, 267(Series C), 322, 1968.
Aromatic Pinacols as Polymerization Initiators, Braun et al, Ind. Ing. Chem., Prod. Res. Develop., vol. 10, No. 4, 387, (1971).
Aromatische Pinakole als Polymerisationsinitiatores, Braun et al, Angew. Makromol. Chem., 6(68), 186, (1969).
Polymerisationsauslosung mit substituierten Ethanen, 1, Polymerisation von Methylmethacrylat mit 1,1,2,2-Tetraphenyl-1,2-diphenoxyethan, Bledski et al, Makromol. Chem., 182, 1047, (1981).
Polymerisationsauslosung mit substituierten Ethanen, 5, Polymerisation von verschiedenen Methacrylmonomeren, Bledzki et al, Makromol. Chem., 184, (1983).
Chem. Abstracts, Wolfers et al, German 2,632,294, (1/19/78) to Bayer.

*Primary Examiner*—Paul F. Shaver
*Attorney, Agent, or Firm*—William A. Teoli; James C. Davis, Jr.; James Magee, Jr.

[57] ABSTRACT

Free-radical initiators are provided in the form of silylethers of arylpinacols. An aryl ketone is reacted with a monohalo- or dihalosilane having at least one olefinically unsaturated organic radical attached to silicon in the presence of an active metal reducing agent, such as magnesium.

6 Claims, No Drawings

FREE-RADICAL INITIATORS AND METHOD FOR MAKING

CROSS REFERENCE TO RELATED APPLICATIONS

Reference is made to my copending application Ser. No. 667,929, for Method for Making Silicone-Organic Block Polymers and Products Obtained Therefrom, filed Nov. 2, 1984 and assigned to the same assignee as the present invention and incorporated herein by reference.

BACKGROUND OF THE INVENTION

Prior to the present invention, benzopinacol and other tetraarylethanes having the formulas $$(C_6H_5)_2C\text{---}C(C_6H_5)_2$$
$$\phantom{(C_6H_5)_2}|\phantom{\text{---}}|$$
$$\phantom{(C_6H_5)_2}CN\phantom{-}CN$$

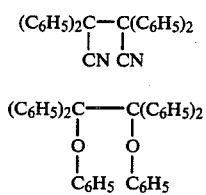

were used as high temperature free radical initiators for the polymerization of vinyl monomers. Additional free radical initiators useful for vinyl monomer polymerization are the corresponding trialkylsilylether derivatives of benzopinacol shown by the formula,

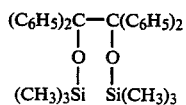

disclosed by Rudolph et al, U.S. Pat. Nos. 3,391,355 and Vio, 3,792,126. Oligomeric silyl pinacoles also are shown to be useful as free radical vinyl monomer initiators by Wolfers et al, Offenlegungsschrift No. 2,632,294 and Reuter et al, Offenlegungsschrift No. 3,151,444.

Although the aforedescribed aryl pinacols and silyl derivatives thereof are useful as free radical initiators to effect the polymerization of a variety of free-radical polymerizable organic monomers, such as styrene, methylmethacrylate, etc. these free-radical initiators cannot be used to effect the polymerization of organic monomers in the presence of blocks of polydiorganosiloxane to provide for the production of silicone-organic block polymers.

As taught in my copending application Ser. No. 667,929, polydiorganosiloxanes are provided having terminal or intrachain silylpinacol functional groups, which provide for the production of silicone organic block polymers upon thermolysis of such functionalized silicone polymers in the presence of free-radical polymerizable organic monomers. The polydiorganosiloxane having terminal or intrachain silylpinacole groups can be made by effecting reaction between silicon hydride containing polydiorganosiloxane and aliphatically unsaturated silylpinacol ethers as defined hereinafter.

STATEMENT OF THE INVENTION

There is provided by the present invention, free-radical initiators in the form of aliphatically unsaturated silylpinacol ethers having the formulas,

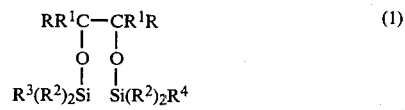

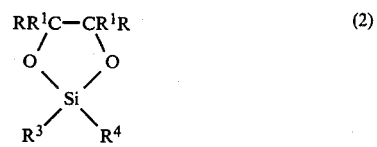

where R and $R^1$ are monovalent radicals selected from $C_{(6-13)}$ aryl hydrocarbon radicals and substituted $C_{(6-13)}$ aryl hydrocarbon radicals, and when joined together and attached to the same carbon atom are selected from divalent aryl radicals having the formula,

$R^2$ is a monovalent radical selected from hydrogen, $C_{(1-8)}$ alkyl, $C_{(1-8)}$ haloalkyl, $C_{(1-8)}$ alkoxy or $C_{(6-13)}$ aryl, $R^3$ is selected from $C_{(2-20)}$ aliphatically unsaturated hydrocarbon radicals, substituted $C_{(2-20)}$ aliphatically unsaturated monovalent hydrocarbon radicals, $C_{(4-20)}$ cycloaliphatic unsaturated hydrocarbon radicals and substituted $C_{(4-20)}$ cycloaliphatic unsaturated hydrocarbon radicals and $R^4$ is selected from $R^2$ radicals and $R^3$ radicals and $R^5$ and $R^6$ are selected from divalent $C_{(6-13)}$ aryl hydrocarbon radicals and substituted $C_{(6-13)}$ aryl hydrocarbon radicals, X is selected from —O—, —S—, —CH$_2$— and $$\overset{\overset{\displaystyle O}{\|}}{C},$$

and a is 0 or 1.

Radicals included within R and $R^1$ of formulas 1 and 2 are, for example, phenyl, tolyl, xylyl, naphthyl, chlorophenyl, methoxyphenyl, nitrophenyl, etc. Radicals included within $R^2$ of formulas 1 and 2 are, for example, $C_{(1-8)}$ alkyl such as methyl, ethyl, propyl, butyl, etc.; haloalkyl, alkoxyalkyl and aryl such as phenyl, tolyl, xylyl, napthyl, etc. Radicals included within $R^3$ are, for example, vinyl, allyl, cyclohexenyl, cyclopentenyl, etc. Radicals included within $R^5$ and $R^6$ are phenylene, tolylene, xylylene, naphthalene and substituted derivatives thereof.

Among the aliphatically unsaturated silylpinacol ethers as shown by formulas (1) and (2), there are included

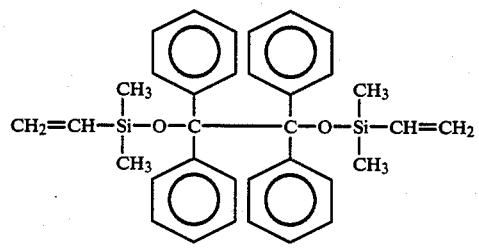

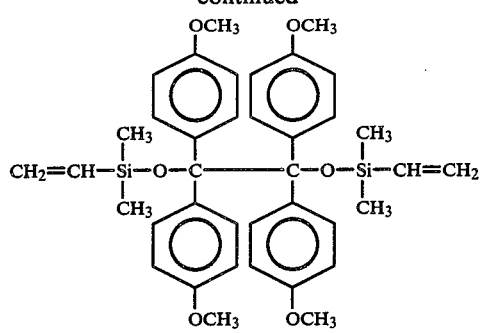

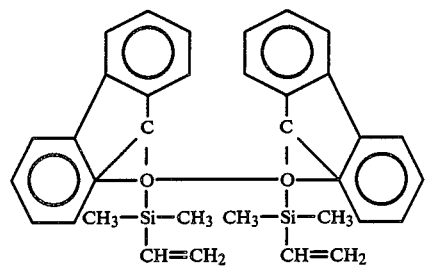

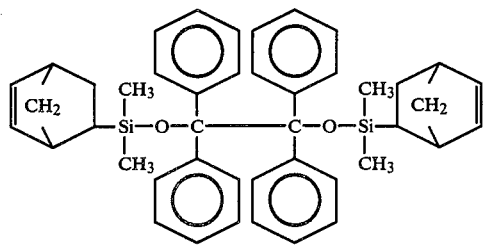

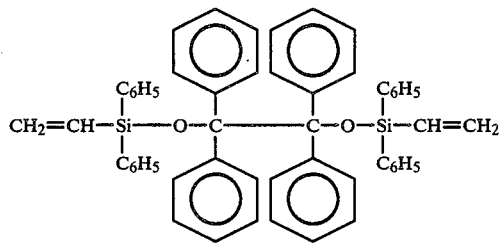

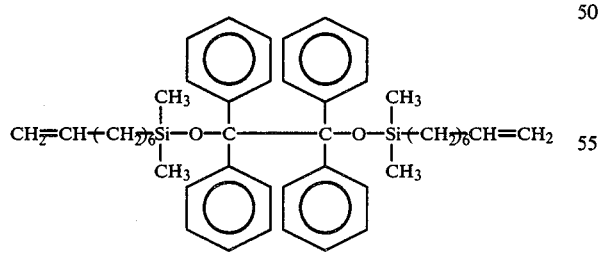

Free-radical initiators shown by formula (1) can be made by effecting reaction between an appropriate ketone with an aliphatically unsaturated monohalosilane in the presence of an active metal reducing agent, such as magnesium as shown by the following equation

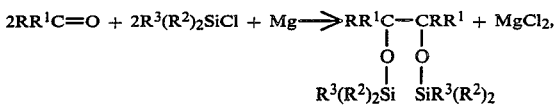

where R, $R^1$, $R^2$ and $R^3$ are as previously defined.

The use of a promotor, such as N,N,N',N'-tetramethylurea, hexamethylphosphortriamide, biphenyl, naphthalene, anthracene is often desired to provide an increase in the rate of the reactions.

A similar procedure can be used for preparing the cyclic silicon containing pinacolates of formula (2) which require the employment of a dihalo aliphatically unsaturated silane in combination with a ketone as shown by the following equation

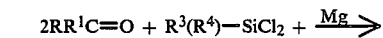

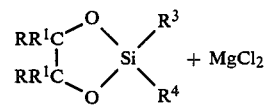

Solvents which may be employed during the course of this reaction are, for example, tetrahydrofuran, dioxane, 1,2-dimethoxyethane, toluene, xylene, benzene, hexamethylphosphortriamide, and N,N,N',N'-tetramethylurea.

Typical cyclic silylpinacolates included within formula (2) are as follows:

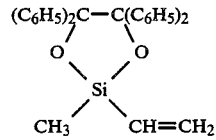

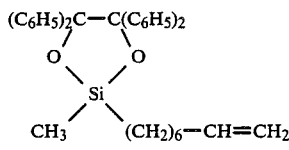

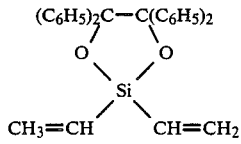

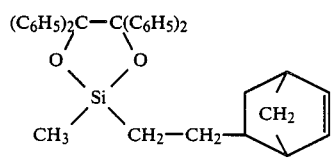

-continued

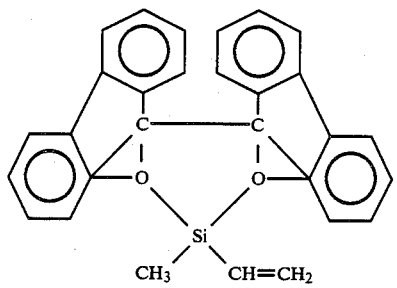

In order that those skilled in the art will be better able to practice the invention, the following examples are given by way of illustration and not by way of limitation. All parts are by weight.

EXAMPLE 1

Into a 1000 ml. round bottom flask equipped with a thermometer, reflux condenser and magnetic stirrer were placed 91.0 g (0.5 mol) benzophenone, 6.0 g (0.25 mol) magnesium metal (30 mesh), 250 ml. dry tetrahydrofuran and 15 ml. N,N,N',N'-tetramethylurea. To this mixture were added dropwise 60.5 g (0.6 mol) dimethylvinylchlorosilane. An exothermic reaction was noted with the temperature rising gradually to 50° C. The reaction mixture was kept at this temperature with the aid of a water bath. After the exothermic portion of the reaction had subsided, the reaction mixture was heated to 47° C. for 4 hours and then allowed to stand at room temperature overnight. The solvent was removed with the aid of a rotary evaporator and the yellow oil dissolved in chloroform. The inorganic precipitate was removed by filtration and the product obtained was recrystallized twice from ethanol. The yield of colorless product obtained having a melting point of 135°–140° C. was 56.3 g or 43.1% theory. The product was bis(dimethylvinylsilyl)benzopinacolate having the formula

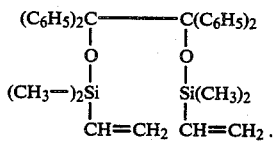

The identity of the compound was confirmed by elemental analysis; Calculated: C; 76.40%, H; 7.12%, Si; 10.49%. Found: C; 75.9%, H; 7.20%, Si; 10.70%.

EXAMPLE 2

To a 500 ml. round bottomed flask there were added 90.1 g (0.5 mol) 9-fluorenone, 15 ml. N,N,N',N'-tetramethylurea, 210 ml. dry freshly distilled tetrahydrofuran and 6 g (0.25 mol) magnesium metal powder. The reaction vessel was fitted with a magnetic stirrer, reflux condenser, thermometer and nitrogen inlet. Nitrogen was bubbled through the reaction mixture for 15 minutes and then 60.5 g (0.56 mol) dimethylvinylchlorosilane were added dropwise by means of the dropping funnel. An exothermic reaction occurred with a change in color which proceeded from clear to yellow to orange. The reaction vessel was placed in a water bath to keep the temperature between 30°–35° C. After addition had been completed (~45 min.), the reaction vessel was allowed to stir overnight at room temperature. The reaction mixture which contained a large amount of crystals was stripped of solvent on a rotary evaporator. Approximately 200 ml. chloroform was added and the reaction mixture was filtered to remove the inorganic magnesium salt. The chloroform was stripped off leaving a solid orange product which was recrystallized from boiling absolute ethanol. On cooling, crystals were obtained which were recrystallized a second time in the same manner. There were obtained in two crops an overall yield of 40% of the silyl pinacolate with a melting point of 210°–212° C. and the following structure as confirmed by means of NMR and the elemental analysis listed below:

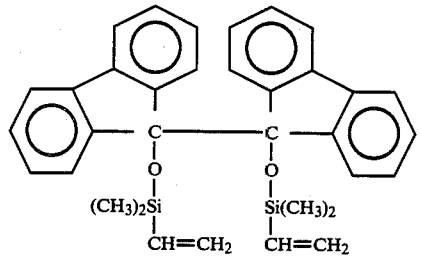

|  | Calc: | Found: |
| --- | --- | --- |
| % C | 79.93 | 76.8 |
| % H | 6.46 | 6.50 |
| % Si | 10.58 | 10.32 |

EXAMPLE 3

Into a 1000 ml. round bottomed flask equipped with a reflux condenser, nitrogen inlet and a magnetic stirrer were placed 72.8 g (0.4 mol) benzophenone, 4.8 g (0.2 mol) magnesium and 200 ml. tetrahydrofuran. To this reaction mixture there were added 28.2 g (0.2 mol) methylvinyldichlorosilane and 15 ml. N,N,N',N'-tetramethylurea. The reaction mixture was heated to start the exothermic reaction. After the exotherm had subsided, the mixture was heated at 50° C. for 2.5 hours then allowed to stand overnight at room temperature. The tetrahydrofuran was removed under reduced pressure and the residue dissolved in chloroform. The resulting mixture was filtered and removed the insoluble inorganic magnesium salts and the solvent again removed under reduced pressure. An oil was obtained which yielded a crystalline product upon recrystallization from ethanol. A total of 50 g product having a melting point of 135°–137° C., an elemental analysis for silicon of 6.71% (theory 6.47%) and a $^1$H NMR in agreement with the following structure

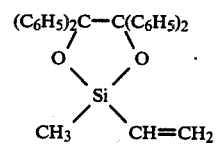

This compound had a melting point of 135°–137° C. and the following elemental analysis:

|  | Calc: | Found: |
| --- | --- | --- |
| % C | 82.45 | 79.2 |
| % H | 5.29 | 5.30 |

-continued

| | Calc: | Found: |
|---|---|---|
| % Si | 3.70 | 3.65 |

EXAMPLE 4

Combined together in a 500 ml. round bottomed flask were 36.4 g (0.2 mol) benzophenone, 2.4 g (0.1 mol) magnesium metal powder, 100 ml. tetrahydrofuran 22.4 g (0.1 mol) 7-octenylmethyldichlorosilane and 10 ml. N,N,N',N'-tetramethylurea. The reaction flask was fitted with a magnetic stirrer, reflux condenser and drying tube. On mixing, an exothermic reaction proceeded spontaneously and the temperature of the reaction mixture was kept below 60° C. with the aid of a water bath. After the exothermic reaction had subsided, the reaction vessel was heated at 50° C. for 1 hour. Under reduced pressure the tetrahydrofuran was removed and about 100 ml. chloroform was added. The inorganic magnesium salts were removed by filtration and the chloroform was stripped off. A pale yellow oil remained which was dissolved in petroleum ether, filtered to remove the small amount of insoluble white impurities and then stripped once again. The product was further purified by several washings with methanol. The $^1$H NMR spectrum was consistent with the structure shown below.

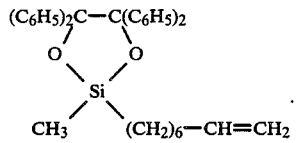

Although the above examples are directed to only a few of the very many free radical initiators which can be made in accordance with the present invention, it should be understood that the present invention is directed to a much broader variety of free radical initiators as shown by formulas (1) and (2).

What I claim as new and desire to secure by Letters Patent of the United States is:

1. Free-radical initiators selected from the class consisting of

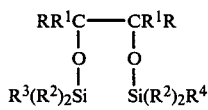

and

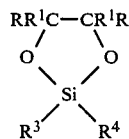

where R and R$^1$ are monovalent radicals selected from C$_{(6-13)}$ aryl hydrocarbon radicals and substituted C$_{(6-13)}$ aryl hydrocarbon radicals, and when joined together and attached to the same carbon atom are selected from divalent aryl radicals having the formula,

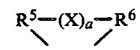

R$^2$ is a monovalent radical selected from hydrogen, C$_{(1-8)}$ alkyl, C$_{(1-8)}$ haloalkyl, C$_{(1-8)}$ alkoxy or C$_{(6-13)}$ aryl, R$^3$ is selected from C$_{(2-20)}$ aliphatically unsaturated hydrocarbon radicals, substituted C$_{(2-20)}$ aliphatically unsaturated monovalent hydrocarbon radicals, C$_{(4-20)}$ cycloaliphatic unsaturated hydrocarbon radicals and substituted C$_{(4-20)}$ cycloaliphatic unsaturated hydrocarbon radicals and R$^4$ is selected from R$^2$ radicals and R$^3$ radicals and R$^5$ and R$^6$ are selected from divalent C$_{(6-13)}$ aryl hydrocarbon radicals and substituted C$_{(6-13)}$ aryl hydrocarbon radicals, X is selected from —O—, —S—, —CH$_2$— and

and a is 0 or 1.

2. The compound

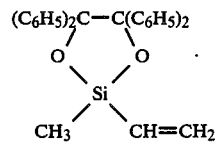

3. The compound

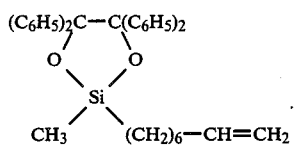

4. The compound

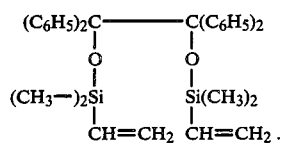

5. The compound

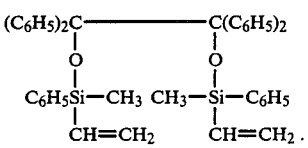

6. The compound

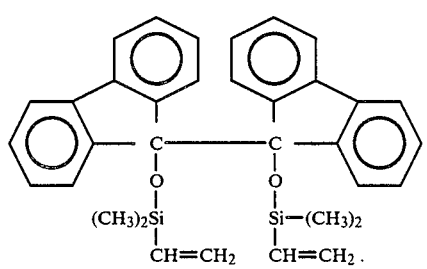

* * * * *